US011445890B2

(12) United States Patent
Levinson

(10) Patent No.: US 11,445,890 B2
(45) Date of Patent: Sep. 20, 2022

(54) MODULAR ENDOSCOPE

(71) Applicant: David M Schreck, San Jose, CA (US)

(72) Inventor: Marc A Levinson, Larkspur, CA (US)

( * ) Notice: Subject to any disclaimer, the term of this patent is extended or adjusted under 35 U.S.C. 154(b) by 88 days.

(21) Appl. No.: 15/731,905

(22) Filed: Aug. 17, 2017

(65) Prior Publication Data

US 2021/0145257 A1     May 20, 2021

(51) Int. Cl.
   *A61B 1/00*     (2006.01)
   *A61B 1/06*     (2006.01)
   *A61B 1/05*     (2006.01)

(52) U.S. Cl.
   CPC ...... *A61B 1/00105* (2013.01); *A61B 1/00016* (2013.01); *A61B 1/00027* (2013.01); *A61B 1/00066* (2013.01); *A61B 1/00112* (2013.01); *A61B 1/00121* (2013.01); *A61B 1/00128* (2013.01); *A61B 1/00131* (2013.01); *A61B 1/00135* (2013.01); *A61B 1/05* (2013.01); *A61B 1/0684* (2013.01)

(58) Field of Classification Search
CPC combination set(s) only.
See application file for complete search history.

(56) References Cited

U.S. PATENT DOCUMENTS

| | | | | |
|---|---|---|---|---|
| 5,125,394 A * | 6/1992 | Chatenever | ............ | G03B 17/48 600/112 |
| 5,205,280 A * | 4/1993 | Dennison, Jr. | ............ | A61B 1/04 348/75 |
| 5,291,010 A * | 3/1994 | Tsuji | ............ | A61B 1/051 250/208.1 |
| 5,311,859 A * | 5/1994 | Monroe | ............ | A61B 1/042 348/75 |
| 5,813,996 A * | 9/1998 | St. Germain | ..... | A61M 25/0905 604/533 |
| 5,895,350 A * | 4/1999 | Hori | ............ | A61B 1/0607 600/167 |
| 5,984,861 A * | 11/1999 | Crowley | ............ | A61B 5/0071 600/175 |
| 6,001,058 A * | 12/1999 | Sano | ............ | A61B 1/07 600/132 |
| 6,004,263 A * | 12/1999 | Nakaichi | ............ | A61B 1/00165 600/120 |
| 6,554,765 B1 * | 4/2003 | Yarush | ............ | A61B 1/00039 348/73 |
| 6,960,161 B2 * | 11/2005 | Amling | ............ | A61B 1/00119 600/110 |
| 7,214,183 B2 * | 5/2007 | Miyake | ............ | A61B 1/00039 600/104 |
| 7,399,275 B2 * | 7/2008 | Goldfain | ............ | A61B 1/00188 600/112 |
| 8,029,439 B2 * | 10/2011 | Todd | ............ | A61B 1/0684 600/178 |
| 8,702,602 B2 * | 4/2014 | Berci | ............ | A61B 90/361 600/249 |

(Continued)

*Primary Examiner* — Alexandra L Newton
*Assistant Examiner* — Shankar Raj Ghimire
(74) *Attorney, Agent, or Firm* — Dana legal services; Jubin Dana

(57) ABSTRACT

A modular endoscope including a handle and sheath that may be coupled or uncoupled. The tip of the sheath distal from the location where it is coupled to the handle includes an illumination element, an image capture element and a deflection element, allowing the distal tip to be pointed in a selected direction.

13 Claims, 10 Drawing Sheets

(56) References Cited

U.S. PATENT DOCUMENTS

| | | | |
|---|---|---|---|
| 9,517,184 B2* | 12/2016 | Branconier | A61M 13/003 |
| 10,051,166 B2* | 8/2018 | Duckett, III | A61B 1/07 |
| 10,163,309 B1* | 12/2018 | Shelton, IV | H02J 7/00 |
| 10,729,315 B2* | 8/2020 | Harrah | A61B 1/00101 |
| 2004/0054254 A1* | 3/2004 | Miyake | A61B 1/00052 |
| | | | 600/104 |
| 2004/0260303 A1* | 12/2004 | Garrison | A61B 17/8816 |
| | | | 606/92 |
| 2006/0173245 A1* | 8/2006 | Todd | A61B 1/07 |
| | | | 600/178 |
| 2006/0287576 A1* | 12/2006 | Tsuji | A61B 1/00105 |
| | | | 600/132 |
| 2008/0125628 A1* | 5/2008 | Ueno | A61B 1/0016 |
| | | | 600/130 |
| 2008/0214896 A1* | 9/2008 | Krupa | A61B 1/00105 |
| | | | 600/136 |
| 2012/0004503 A1* | 1/2012 | Kawaura | A61B 1/00087 |
| | | | 600/104 |
| 2012/0100729 A1* | 4/2012 | Edidin | H01R 13/622 |
| | | | 439/38 |
| 2012/0238813 A1* | 9/2012 | Ashida | A61B 1/0125 |
| | | | 600/114 |
| 2013/0144123 A1* | 6/2013 | Nakamura | A61B 1/0016 |
| | | | 600/114 |
| 2013/0197307 A1* | 8/2013 | Ashida | A61B 1/00006 |
| | | | 600/114 |
| 2013/0261391 A1* | 10/2013 | Dejima | A61B 1/0016 |
| | | | 600/114 |
| 2014/0012084 A1* | 1/2014 | Naito | A61M 25/0113 |
| | | | 600/114 |
| 2014/0107416 A1* | 4/2014 | Birnkrant | A61B 1/00057 |
| | | | 600/110 |
| 2014/0296633 A1* | 10/2014 | Gumbs | A61B 1/00052 |
| | | | 600/109 |
| 2016/0038012 A1* | 2/2016 | McMahon | A61B 1/00016 |
| | | | 600/210 |
| 2016/0128550 A1* | 5/2016 | Laser | A61B 1/00126 |
| | | | 600/111 |

\* cited by examiner

DETAIL A

MODULAR ENDOSCOPE

CROSS-REFERENCE TO RELATED APPLICATION

This patent claims priority from provisional patent application No. 62/392,752 filed Jun. 10, 2016 the entire disclosure of which is incorporated herein by reference.

TECHNICAL FIELD

The present invention relates to medical devices and more specifically to modular endoscopes.

BACKGROUND

Endoscopes are medical devices used to visually observe an internal body anatomy for the monitoring and/or treatment of medical conditions. The scope will include a handle that controls the elements of the scope. Endoscopes generally include the following elements:
1. An illumination device terminating at the tip allowing illumination of an internal area.
2. An imaging optic also at the tip allowing image capture of the internal area. The image sensor may be an optical fiber and rod lens scope design.
3. An auxiliary channel. This channel allows, for example, introduction of a liquid (such as saline or a liquid containing a pharmaceutical compound) to be added. Alternatively, the auxiliary channel could allow introduction of a needle for a biopsy or other tool. Some endoscopes will not include an auxiliary channel.
   Endoscopes are used in a number of medical specialties, including urology, gynecology, general surgery, intubation, arthroscopy gastroenterology and otolaryngology. Additional specialties include neurosurgery, spine surgery, cardiology, cardiovascular surgery, pulmonology.

Endoscopes present a number of technical challenges. A first technical challenge is sterilization. The instrument will be introduced into a patient's body and thus requires sterilization. Although some surgical tools can be inexpensively heat sterilized, an endoscope which is made of differing materials, is not adaptable to heat sterilization and instead must be sterilized by low temperature chemicals or other means. A second technical challenge is reliability. If the sterilization process degrades the performance or reliability of an endoscope, current practice is to simply use the endoscope a single time, when the device is provided in a sterile, sealed package. However, this presents a third challenge, cost, which is greatly increased if an entire endoscope must be discarded after a single use. It is an object of the embodiments to improve on the current technology to address these technical challenges.

SUMMARY

The present described embodiments have a number of advantages, including cost reduction, simplification of sterility, and reliability. The embodiments describe a modular endoscope that includes a handle and a sheath. The sheath has a proximal coupling end that may be joined to the handle and a distal tip end. The sheath may be rigid, semi-rigid, or flexible, as selected by requirement for a procedure. A coupling mechanism joins the handle to the sheath. An image sensor is mounted on the tip of the sheath. The image sensor could be connected by a wired connection through the sheath, to the handle, and then to a display. Alternatively, the image sensor may be wireless, allowing still images or video to be collected directly onto a system external to the endoscope. The tip end also includes an illumination source. This illumination source may be an LED at the tip of the sheath (along with a power source). Alternatively, the illumination source may be an LED in the handle of the endoscope or in the proximal end of the sheath and an optical fiber bringing light from the LED to the tip to illuminate the area in front of the tip of the sheath. The tip also includes a tip deflecting mechanism which allows the tip to be angularly deflected to allow a wider view of an internal area. Depending on the embodied design, this deflection could be up to 280 degrees. The endoscope sheath may include an auxiliary channel having a first end proximate to the coupling end of the sheath, and a second end terminating to the tip end of the sheath. This auxiliary channel allows a fluid or a surgical tool or component to be introduced through to the tip end of the sheath.

DETAILED DESCRIPTIONS

Figure 1:
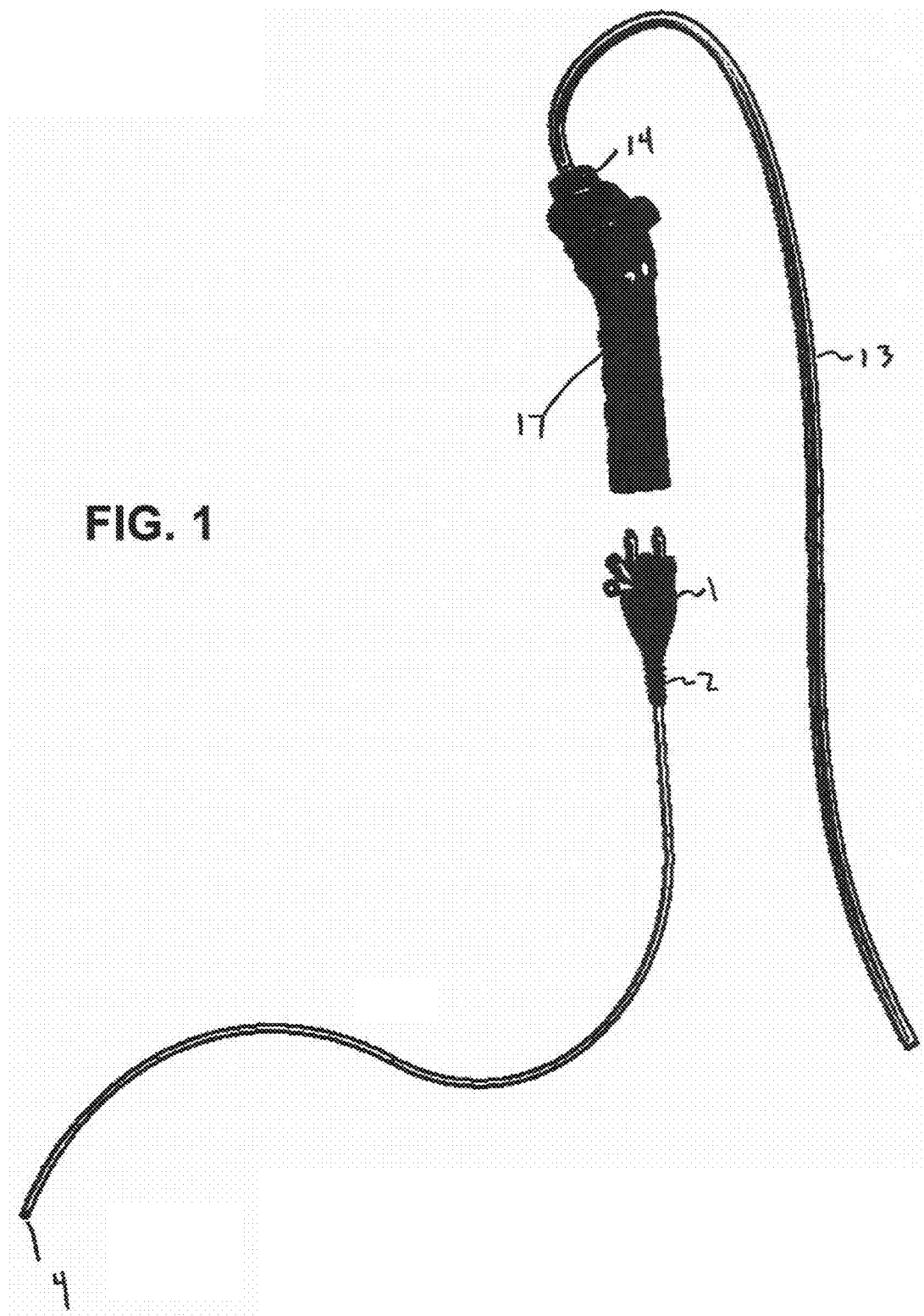
FIG. 1 is a side view of a handle and sheath embodiment.

With reference to FIG. 1, a complete endoscope is comprised of a handle 17 and a sheath 1. The endoscope's handle 17 couples to a sheath 1 in this embodiment allowing for sheath tip 4 control (i.e., active scope tip deflection). The handle locking knob 14 locks the handle onto the sheath once the devices adjoined at the coupling mechanism interface. On the sheath, near the coupling end is a strain relief 2, to facilitate support of the bending of the sheath. The handle control cable 13 attaches the handle to a computer or cell and power source, which is then connected (wired or wirelessly) to a monitor or display. The sheath terminates in tip end 4.

This mating also allows for powering of the camera/visualization scope function and the lighting (i.e., Light Emitting Diodes (LED's)). As mentioned previously, the sheath maybe rigid (no appreciable bending), semi-rigid (bending resistant, but sight bend possible), or flexible (able to bend). The tip 4 of the sheath (i.e., scope tip end) will be capable of deflecting in one or more directions and up to 280° depending on endoscope design. For both flexible ureteroscopes and the hysteroscope, the tip will deflect in two opposing directions in the same plane. There will be times when the user will need to rotate the tip which the user will do by twisting the handle. This will rotate the sheath in a close ratio of 1:1 with the handle.

Figure 2:
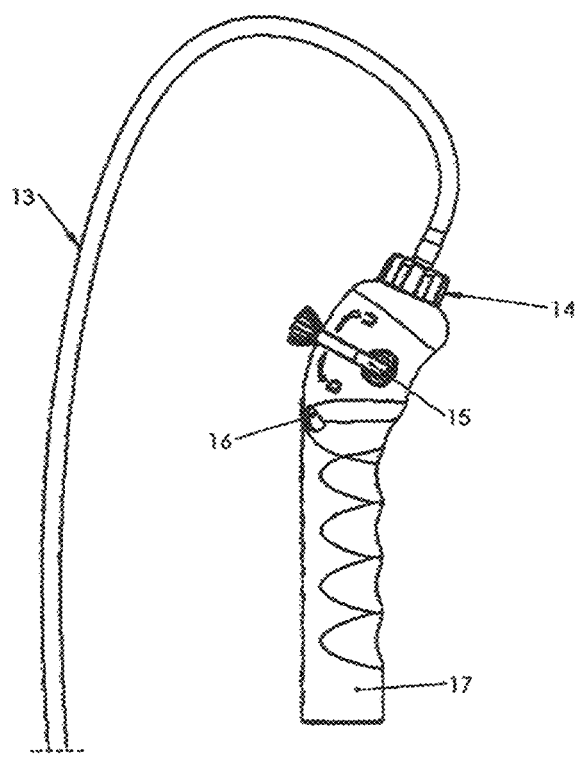
FIG. 2 is a side view of a handle embodiment.

With reference to FIG. 2 The handle 17 is shown with sheath assembly locking knob 14. Rotation of this knob allows mechanical connection of the handle 17 to the sheath as shown in FIG. 1. A steering actuation lever 15 allows angular aiming of the tip 4 of the sheath 1, as shown in FIG. 1. Electronic control buttons 16 allow activation of various elements of the endoscope. In one embodiments three such buttons are used, one to control power to the lighting source (e.g. LED), one to capture still pictures, and one to capture video.

Figure 3:
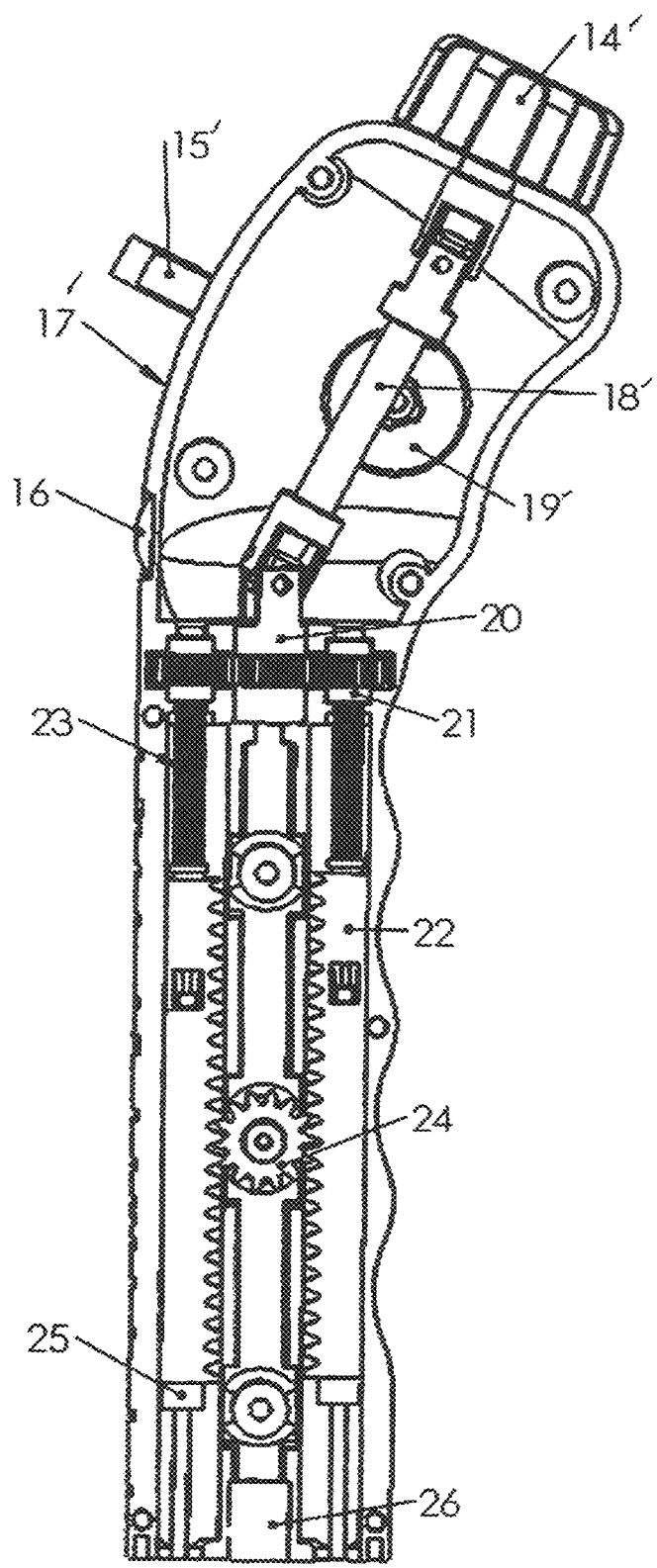
FIG. 3 is a cross sectional view of a handle embodiment.

With reference to FIG. 3, the handle 17 is shown in cross section. The sheath tip steering actuation lever 15 is linked to steering wire pull wheel 19. On pull wheel 19 is mounted gear rack pull wire 27. The ends of wire 27 are affixed at the tip end of the sheath. Actuation of lever 15 moves pull wheel 19, pulling on an end of pull rack gear wire 27. This allows angular deflection of the tip of the sheath in a plane.

The handle locking knob 14 is joined to locking joint assembly 18 connected to locking gear joint 20. Rotation of gear joint 20 engages sliding spline gear 21 on locking spline 23. This moves gear rack 22 on rack following gear 24 locking rack spline sleeve 25 into the sheath. At the end of handle 17 is the handle side electrical connector 26, in electrical connection with buttons 16 and to the existing cable that connects to the camera control unit (CCU) and power.

Figure 4:
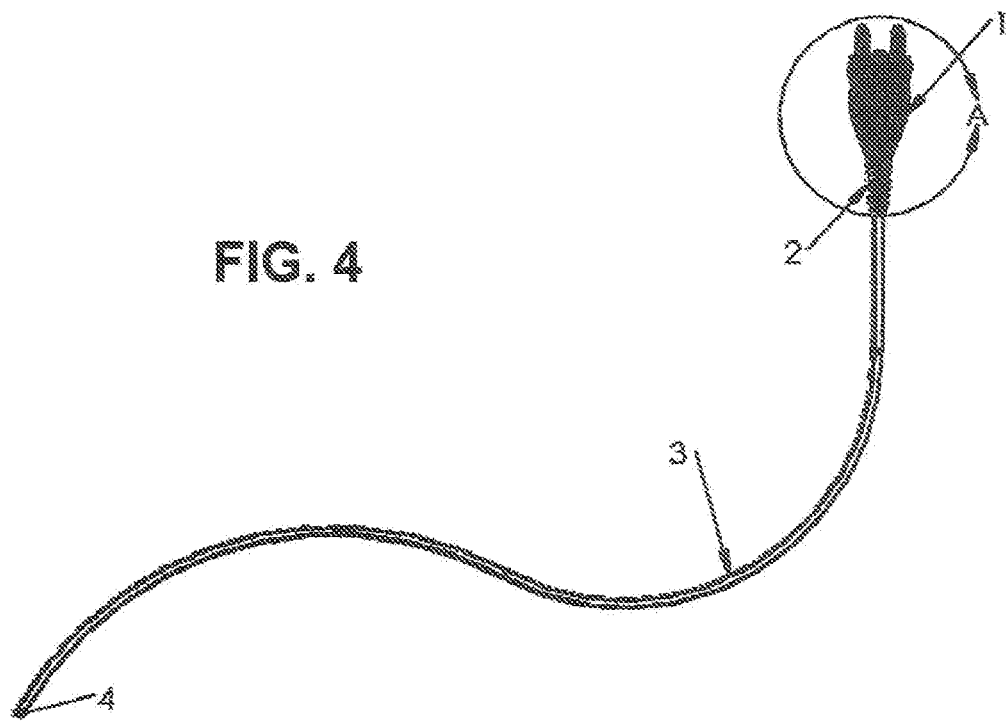
FIG. 4 is a side view of a sheath.
Figure 5:
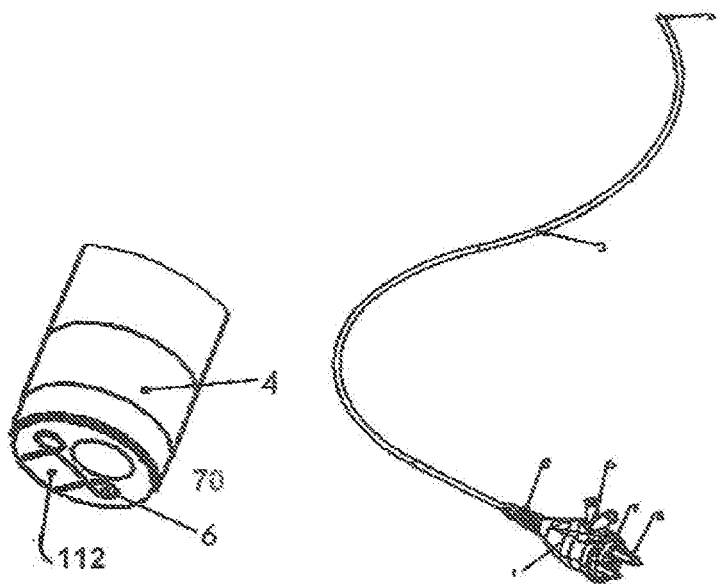
FIG. 5 is a detail of the tip end of the sheath.
Figure 7A:
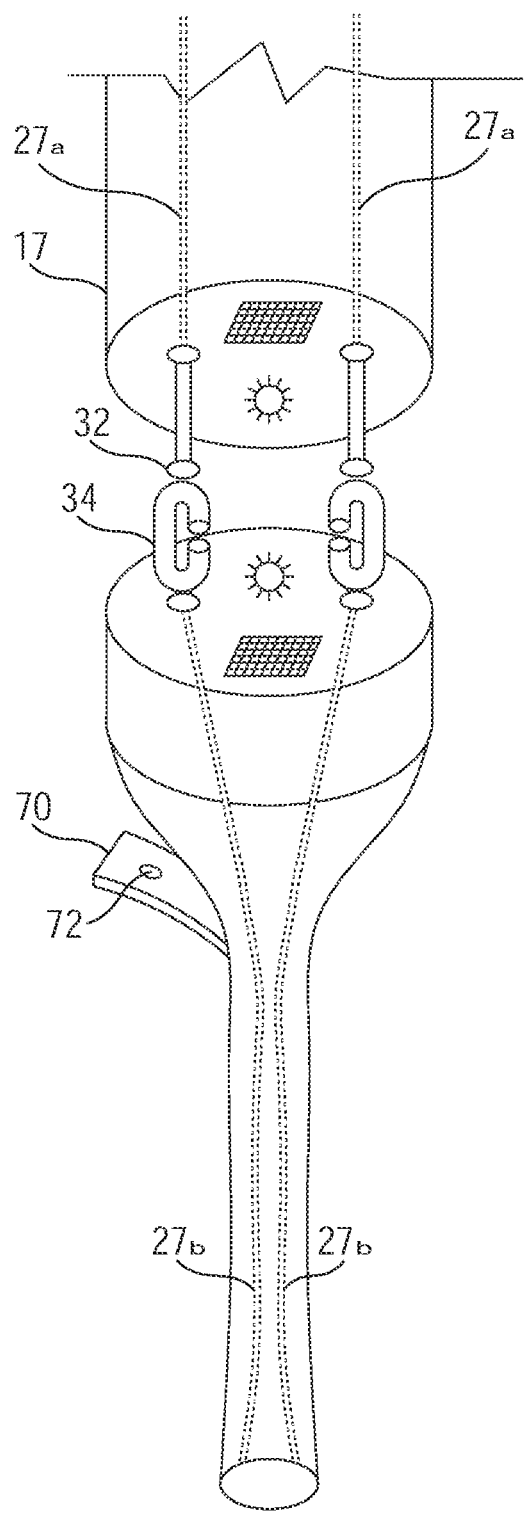
FIG. 7A is a side perspective view of a ball and socket connection embodiment between the handle and sheath.

With reference to FIG. 4, the sheath 1 is shown with strain relief 2 at the end of the connector portion, the flexible reinforced shaft body 3 of sheath 1 and a terminal tip 4. The terminal tip 4 is shown in FIG. 5, having a terminal light fiber bundles 6 and a camera sensor 112. The end of auxiliary channel 70 is also shown. This channel allows irrigation or use of a surgical tool, as shown in FIG. 7A as auxiliary channel 70.

In addition, the Shaft/Sheath may incorporate a single or multiple integrated channels to be used for introduction/withdrawal of various surgical tools and/or infusion/evacuation of water or saline/lactate ringer's solution and/or other fluid substances (e.g., drugs).

The endoscope's imaging platform will be produced via an integrated color CMOS sensor (and complementary objective lens) located at the distal end of the sheath tip 4. The processing of the signal will either be completed within the endoscope's body (to include Shaft/Sheath and Handle) that is wired directly to a remote camera processor unit that is connected to a display (i.e., monitor (e.g., integrated small monitor, stand-alone monitor, computer, tablet, cell phone, etc.)) or transmitted wirelessly to a display (i.e., monitor). Light will be produced through either an integrated powered LED(s) placed at the distal end of the endoscope or positioned within the Handle where the emitted light is transmitted down a fiber optic bundle embedded within the Shaft/Sheath exiting the distal tip end of the endoscope. The endoscope will be wired directly to a remote power source (i.e., AC power) or powered by an integrated rechargeable battery for wireless designed endoscopes.

With reference to FIGS. 7A-7E, the connection between handle 17 and sheath 1 is shown. In each embodiment, the gear rack pull wire has a handle wire section 27a and a sheath section 27b. Also these embodiments show an auxiliary channel 70 having an auxiliary channel valve 72.

Figure 6:
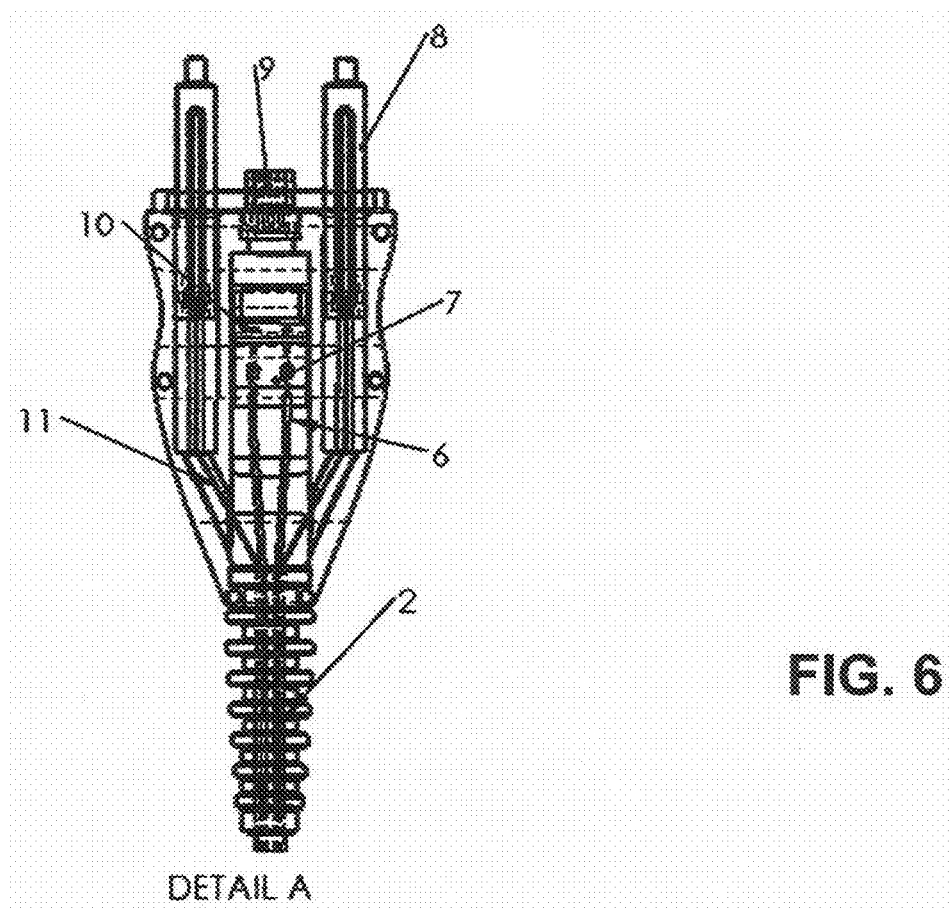
FIG. 6 is a cross section of the coupler proximate end of the sheath (detail A from FIG. 4).
Figure 7B:
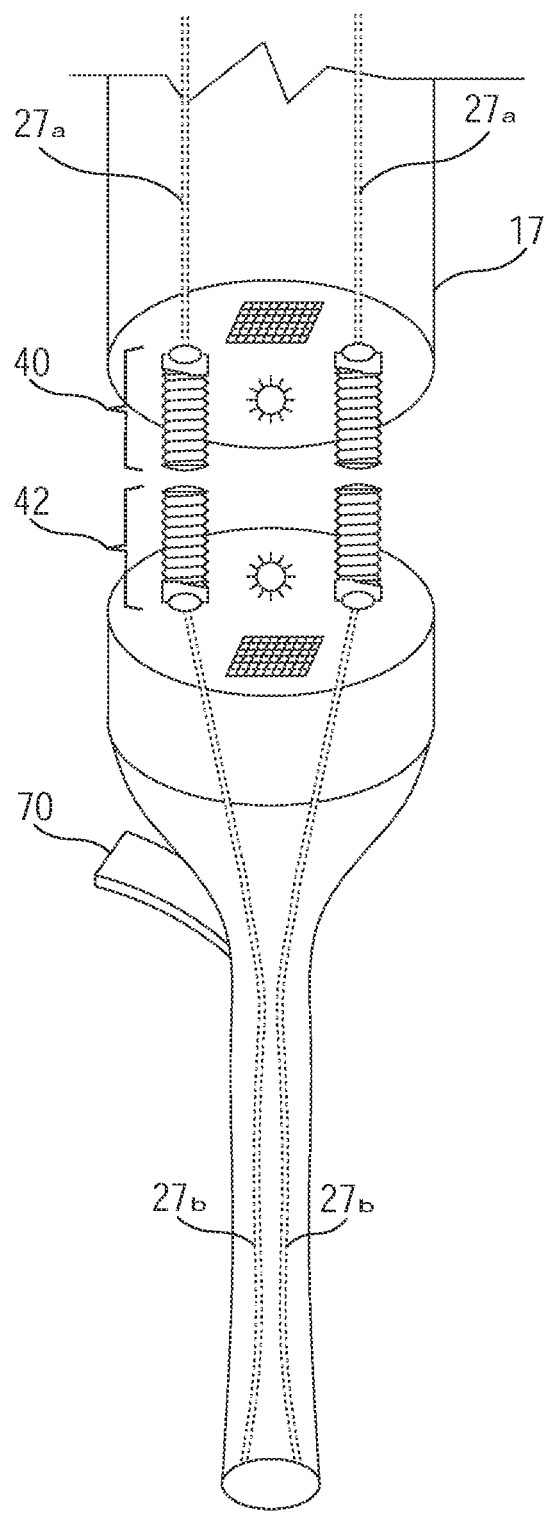
FIG. 7B is a side perspective view of a threaded connection embodiment between the handle and sheath.
Figure 7C:
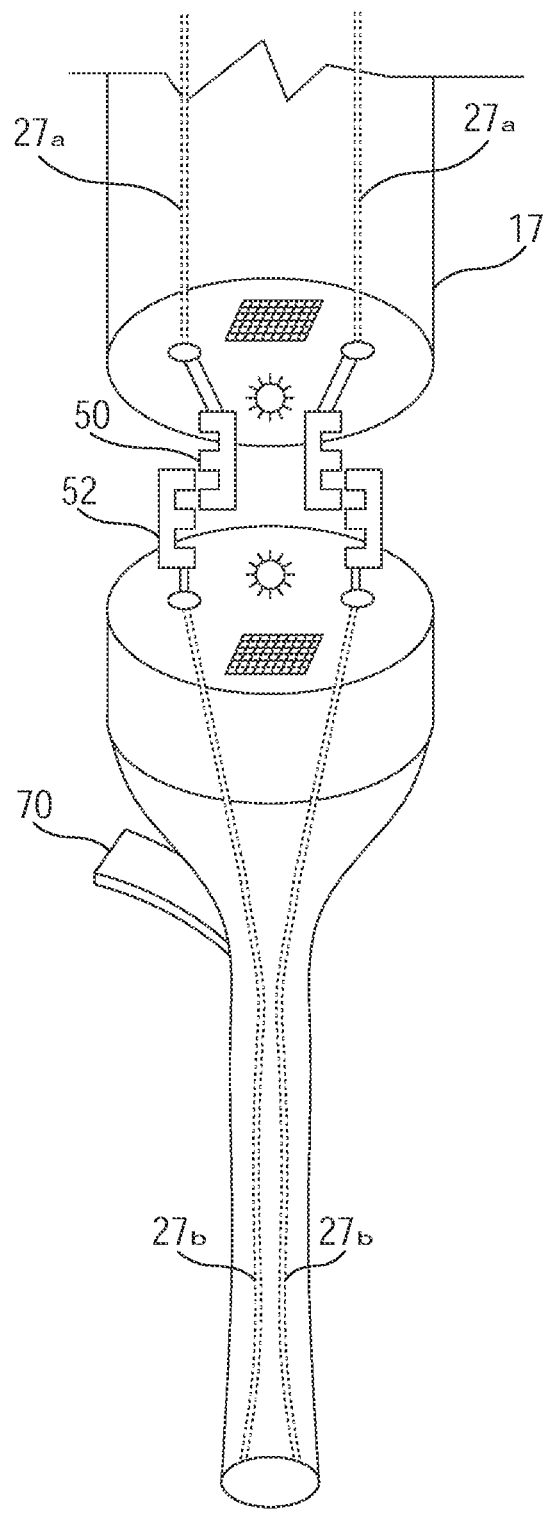
FIG. 7C is a side perspective view of opposing gears connection embodiment between the handle and sheath.
Figure 7D:
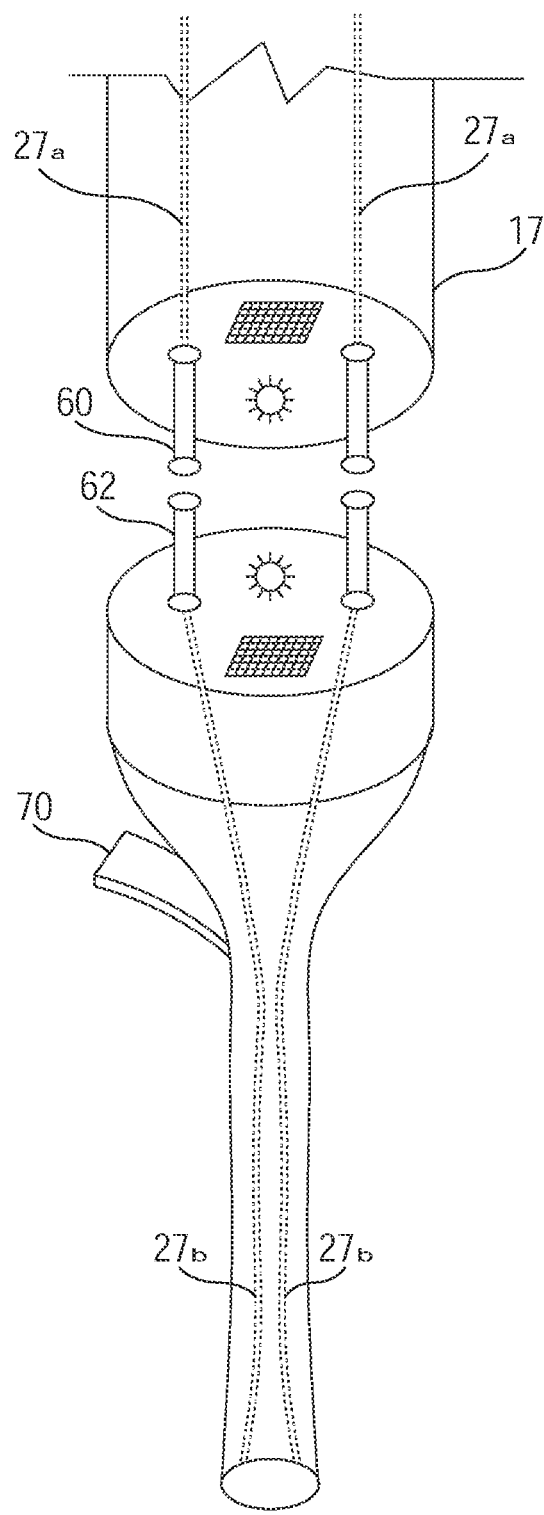
FIG. 7D is a side perspective view of a magnetic coupler connection embodiment between the handle and sheath.
Figure 7E:
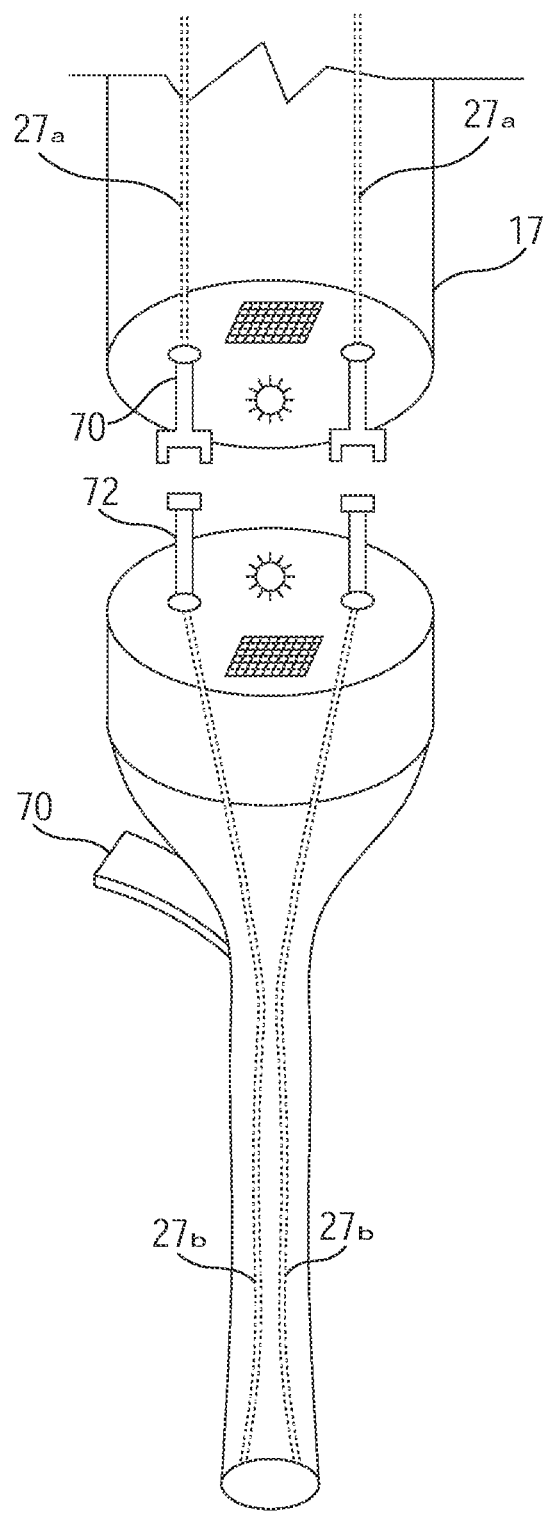
FIG. 7E is a side perspective view of a male/female connection embodiment between the handle and sheath.

In FIG. 7a, a ball 32 is joined to a socket 34. The ball and socket placement is arbitrary, and could be switched from handle or sheath side. FIG. 7b shows a handle threaded connector 40 and a sheath threaded connector 42. FIG. 7c shows a handle gear assembly 50 mating with a sheath gear assembly 52. FIG. 7d shows a handle magnet 60 and a sheath magnet 62. A strong earth magnet, such as Neodynium magnets are preferred. Finally, FIG. 7e shows a locking connection in which a female connector 70 on the handle mates with a male connector 72 on the sheath. As with the ball and socket, the male/female ends may be placed on handle and sheath or sheath and handle. As shown in FIGS. 3 and 6, the handle and sheath can be joined to form a linked instrument, with the connectors illustrated in FIGS. 7a-7e contained within the housing of the instrument. In each connection embodiment shown, the ends of wires 27b are affixed at the tip.

With reference to FIG. 6, the detail of the proximal coupling end of the sheath is shown. Strain relief 2 adds flexibility and strength to this element. The sheath electrical connector 9 allows mating with the handle electrical connector 26 to provide the required power for and signal transmission for the elements (e.g. image sensor and LEDs). The LED support block 7 supports an LED PCB 10 configured to provide light into optical fibers 6. These fibers terminate at the sheath tip, as shown in FIG. 5.

The Handle will house the integrated LED(s) for designs that integrate a light fiber bundle in the Shaft/Sheath. In other designs where no light fiber bundles are used, the LED(s) will be positioned at the distal end or tip of the endoscope. As shown in FIG. 6, the LEDs are positioned in the proximal end of the sheath, and a light fiber is used to carry the light to the distal tip of the sheath.

The steering pull wire 11 is shown within a threaded mating 8. Threaded mating 8 screws into a receiving threaded receptacle on the handle, affixing the handle and sheath together.

To ensure complete endoscope function, there will be between the Handle and the Shaft/Sheath the following connections.

First the embodiment shown will have an electronic connection between the wires emanating from the CMOS sensor of the sheath to the wires from the AC power (or if wireless, a rechargeable battery included on the sheath. LED(s) exiting the handle or proximal end of the sheath will be positioned within a specified/optimized distance to the light fiber bundles within the Shaft/Sheath (Or for endoscopes not utilizing light fiber bundles but with LED(s) positioned at the distal end or tip of the endoscope, a special mating connection will be designed so that the electrical connection between the LED(s) wires within the Shaft/Sheath are mated to the powered wires emanating from the Handle). The power will be supplied by AC power (or if wireless, rechargeable battery).

The novel connection between the angulation wires within the Shaft/Sheath and the angulation wires and controlling actuator of the Handle (as described above with respect to FIGS. 7A-7E) will control the tip deflection of the endoscope once the two components are mated.

The sheath design will be rigid, semi-rigid, or flexible with or without an active endoscope distal end tip deflection. The sheath will incorporate or integrate single or multichanneled depending on endoscope design and application. The CMOS sensor with complementary objective lens will be positioned at the distal end of the endoscope. The LED(s) will also be positioned at the distal end of the endoscope (unless the LED(s) are positioned within the handle or proximal end of the sheath in which case, there will be a minimum of one or more light fiber bundles integrated within the sheath and exiting both ends of the sheath or mated to an LED within the proximal end of the sheath).

All image signals will be processed and transmitted to an integrated display monitor and/or to an external unattached display monitor.

Operation

This endoscope design is a 'plug & play' system. In a wired configuration, select your Handle, choose your Shaft/Sheath for the intended application, snap these two components together, connect to desired display/monitor, and plug into a power source and camera control unit (unless it is a wireless design endoscope). Turn on the system and begin your procedure.

Upon procedure completion, clean and reprocess components according to standard AORN operating room reprocessing procedures or if an office setting, adhere to minimum reprocessing requirements. (If the Shaft/Sheath is disposable, follow standard biohazard disposal standards.)

I claim:

1. A modular endoscope comprising:
a handle having an actuation lever and a coupling mechanism;
a sheath having a coupling end and a tip end, wherein the coupling mechanism comprises a gear and a spline sleeve and locks the handle to the coupling end of the sheath and releasably joins the handle and the coupling end of the sheath;
an illumination source configured to provide light projected from the tip end of the sheath;
an image sensor mounted on the tip end of the sheath, configured to capture image data from in front of the tip end of the sheath; and
an active tip deflecting mechanism including:
a first pair of wires positioned through the sheath, wherein one end of each of the first pair of wires includes a first engaging portion and an opposite end of each of the first pair of wires is connected to the tip end; and
a second pair of wires positioned through the handle, wherein one end of each of the second pair of wires includes a second engaging portion and an opposite end of each of the second pair of wires is connected to the actuation lever,
wherein each one of the first engaging portions connects to one of the second engaging portions thereby allowing the tip deflecting mechanism to extend from the actuation lever of the handle to the tip end of the sheath to allow angular deflection of the tip end of the sheath using the actuation lever at the handle.

2. The endoscope of claim 1, wherein the sheath is rigid up to said tip end, thereby allowing said tip end to deflect.

3. The endoscope of claim 1, wherein the sheath is semi-rigid up to said tip end, thereby allowing said tip end to deflect.

4. The endoscope of claim 1, wherein the sheath is flexible.

5. The endoscope of claim 1, wherein the handle further includes an actuator and the illumination source includes:
an LED at the tip end of the sheath; and
a power source for the LED, wherein the actuator turns on the LED.

6. The endoscope of claim 1, wherein the handle further includes an LED and wherein the illumination source includes:
an optical fiber positioned to conduct light from the LED in the handle to the tip end; and
a window allowing light from the LED in the handle to be projected from the tip end.

7. The endoscope of claim 1, wherein said sheath includes an auxiliary channel having a first end proximate to the coupling end of the sheath, and a second end terminating at the tip end of the sheath, the auxiliary channel allowing fluid or a surgical tool to be introduced through to the tip end of the sheath.

8. The endoscope of claim 1, wherein the active tip deflecting mechanism is configured to allow 280 degree tip deflection.

9. The endoscope of claim 1, wherein the illumination source includes an LED embedded in the tip end of the sheath.

10. The endoscope of claim 1, wherein the first engaging portion and the second engaging portion of the active tip deflecting mechanism are a ball and a socket.

11. The endoscope of claim 1, wherein the first engaging portion and the second engaging portion of the active tip deflecting mechanism are a threaded coupling.

12. The endoscope of claim 1, wherein the first engaging portion and the second engaging portion of the active tip deflecting mechanism are a strong magnetic coupling.

13. The endoscope of claim 1, wherein the first engaging portion and the second engaging portion of the active tip deflecting mechanism are a male and a female mating coupler.

* * * * *